United States Patent [19]

Enomoto et al.

[11] Patent Number: 5,508,202
[45] Date of Patent: Apr. 16, 1996

[54] METHOD OF DETERMINING BLOOD COAGULATION FACTOR XIII ACTIVITY AND KIT OF REAGENTS FOR THE DETERMINATION

[75] Inventors: Masayasu Enomoto, Takatsuki; Masahiro Yamaguchi, Suita, both of Japan

[73] Assignee: Nippon Shoji Kaisha, Ltd., Osaka, Japan

[21] Appl. No.: 232,221

[22] PCT Filed: Sep. 3, 1993

[86] PCT No.: PCT/JP93/01247

§ 371 Date: May 4, 1994

§ 102(e) Date: May 4, 1994

[87] PCT Pub. No.: WO94/07145

PCT Pub. Date: Mar. 31, 1994

[30] Foreign Application Priority Data

Sep. 11, 1992 [JP] Japan .................... 4-243098

[51] Int. Cl.⁶ .................................. G01N 33/86
[52] U.S. Cl. ................ 436/69; 436/166; 422/61
[58] Field of Search ............... 422/73, 61; 436/69, 436/164, 166, 174

[56] References Cited

U.S. PATENT DOCUMENTS

| 3,323,995 | 6/1967 | Lorand . | |
|---|---|---|---|
| 5,204,240 | 4/1993 | Stuber | 436/69 X |
| 5,292,664 | 3/1994 | Fickenscher | 436/69 |

FOREIGN PATENT DOCUMENTS

| 0535799 | 4/1993 | European Pat. Off. . |
| 2622180 | 3/1978 | Germany . |
| 4133946 | 4/1993 | Germany . |
| 58-216959 | 12/1983 | Japan . |
| 59-192961 | 11/1984 | Japan . |
| 63-184061 | 7/1988 | Japan . |
| 1309700 | 12/1989 | Japan . |
| 367173 | 3/1991 | Japan . |
| 560763 | 3/1993 | Japan . |
| 5219993 | 8/1993 | Japan . |

OTHER PUBLICATIONS

Grant, J. "Hackh's Chemical Dictionary" 4th ed., see difinition of Fibrinogen (1969).
Beate Wagner et al, "Determination Of Factor XIII Activity By A New Photometric Assay in Plasma and Platelets of Healthy Blood Donors", Thrombosis Research, vol. 74, No. 2, pp. 169–174, 1994.
Nippon Rinsho, vol. 47, a special 1989 number, pp. 846–848, Aug. 1983.
Rinsho Kensa, pp. 848–853, vol. 27, No. 8, Aug. 1983.
Medical Technology, vol. 13, No. 7, pp. 726–729.
Spellman, Jr., et al., Blood, vol. 50, No. 4 (Oct.), 1977, pp. 619–624.
Muszbek et al., Clinical Chemistry, vol. 31, No. 1, 1985, pp. 35–40.
Laudano et al., Biochemistry, vol. 19, No. 5, 1980, pp. 1013–1019.

Primary Examiner—Jeffrey R. Snay
Attorney, Agent, or Firm—Foley & Lardner

[57] ABSTRACT

An accurate, rapid and simple method of determining blood coagulation factor XIII activity and a kit of reagents therefor are provided. A sample and a fibrin precipitation inhibitor are mixed, or a sample, fibrinogen and a fibrin precipitation inhibitor are mixed; a thrombin solution is added; the fibrin coagulation time is measured in the presence of calcium ion; and the coagulation time is compared with the normal coagulation time. The kit for the determination comprises thrombin, calcium ion and a fibrin precipitation inhibitor, and may be combined with fibrinogen.

6 Claims, 2 Drawing Sheets

METHOD OF DETERMINING BLOOD COAGULATION FACTOR XIII ACTIVITY AND KIT OF REAGENTS FOR THE DETERMINATION

TECHNICAL FIELD

The present invention relates to a method of determining activity of blood coagulation factor XIII (hereinafter referred to as factor XIII) and a kit of reagents for the determination.

BACKGROUND ART

The factor XIII is also referred to as fibrin stabilizing factor. It is a protein playing a part in the promotion of acquiring the resistance to fibrinolysis and forming adhesion carriers of fibroblasts. When activated by thrombin and calcium ion, the factor XIII causes cross-linking reaction between fibrin molecules and between fibrin and other proteins by transglutaminase reaction during the terminal stage of the blood coagulation reaction to form stable fibrin clots and the like. Normally, this protein exists in blood in an inactive form, but when blood coagulation is caused by hemorrhage or the like to form thrombin, it is activated by the action of thrombin and calcium ion to stabilize fibrin.

Therefore, although a normal threshold of blood coagulation time is seen in the case of a decrease or lack in the factor XIII in blood, the resulting fibrin clots are weak and show a tendency to delay healing of wounds in addition to characteristic phenomena such as posthemorrhage and the like. The decrease or lack in the factor XIII are seen in, for example, congenital deficiency, disseminated intravascular coagulation (DIC), serious hepatic diseases, malignant tumor, leukemia, acquirers of a factor XIII inhibitors, major operations or the like. Therefore, the determination of the factor XIII is of importance in diagnosing diseases or evaluating therapeutic effects. It is required to establish a method of determining the factor XIII accurately, quickly and easily.

However, prior art methods of the determination are not satisfactory for this need. The following methods are known as conventional methods of determining the factor XIII: qualitative methods by clot dissolution which test whether clots (fibrin clots) formed by plasma coagulation are soluble in a diluted acid solution (e.g., 1% monochloroacetic acid, etc.) or a urea solution (5–8 mol/l); semiquantitative methods by clot dissolution after antibody neutralization or serial dilution; other immunological methods; quantitative methods by amine uptake utilizing the transglutaminase activity of the active factor XIII (e.g., Nippon Rinsho, vol. 47, a special 1989 number, p. 846–848; Rinsho Kensa, vol. 27, No. 8, p. 848–853 (August 1983)). However, accurate activity of the factor XIII is not determined by qualitative or semiquantitative methods.

Immunological methods wherein an antibody to the factor XIII is used to catch the factor XIII as an antigen (e.g., JP-A 59-192961, JP-A 63-184061) generally need complicated operations and take several hours for the determination. Further, it is problematic in that, because of the determination in terms of an antigenic amount, factor XIII activity in living bodies is not reflected accurately.

As amine uptake methods for the quantitative determination of factor XIII activity, there are the radioisotope method wherein the factor XIII in a sample is activated by thrombin and calcium ion to form the activated factor XIII, followed by incorporation of amine substrates into carbonyl substrates using casein, phenylpropionylthiocholine, butyrylpyrazole or the like as the carbonyl substrate, synthetic substrates such as monodansylcadaverine, putrescine, glycine ethyl ester, histamine or the like as the amine substrate; fluorescence methods (e.g., JP-A 58-216959); the method wherein ammonia formed by amine uptake reaction is introduced to AND or NADP forming reaction using NADH or NADPH and GLDH (glutamate dehydrogenase) and ketoglutarate (Clin. Chem., Vol. 31, No. 1, p. 35–40, 1985; JP-A 1-309700). To inactivate fibrinogen in the sample, these methods need operations of warming at 56° C. for 3 to 4 minutes followed by cooling before the factor XIII is activated. The reaction time for the determination of the activated factor XIII is 10 to 30 minutes, and centrifugal or chromatographic operations are needed after the reaction. Therefore, the operations are complicated and take much time, and there is a problem in the accuracy of the determination. Since the radioisotope method uses radioactive substances and needs a heavy equipment investment and has a severe economical burden.

In the method described in JP-A 1-309700 of the above amine uptake methods, glycine-proline-arginine-proline, a fibrin coagulation inhibitor, is used to remove effects of fibrinogen-fibrin. The formed ammonia is determined using a glutamine-containing peptide such as leucine-leucine-glycine-proline-glycine-glutamine-serine-lysine-valine-iso-leucineglycineamide and a primary amine in the presence of the fibrin coagulation inhibitor. This method costs much because a special peptide is used. Further, many reactions are involved in the determination and errors are likely to be caused. Further, ammonia present in the sample can affect the determination.

OBJECTS OF THE INVENTION

The object of the present invention is to provide an accurate, rapid and simple method of determining factor XIII activity, which does not have the problems of prior art methods, and a kit of reagents for the determination.

The present inventors have intensively studied to achieve the above object. As a result, it has been found that factor XIII activity can be determined by (i) carrying out a series of reactions (i.e., conversion of fibrinogen into fibrin by thrombin; activation of the factor XIII by thrombin and calcium ion; and cross-linking of fibrin by the activated factor XIII to form fibrin clots) in the presence of a fibrin precipitation inhibitor; (ii) determining the coagulation time required for the precipitation of the resulting fibrin clots; and (iii) comparing the time with the normal coagulation time. Thus, the present invention has been completed.

SUMMARY OF THE INVENTION

Figure 1:
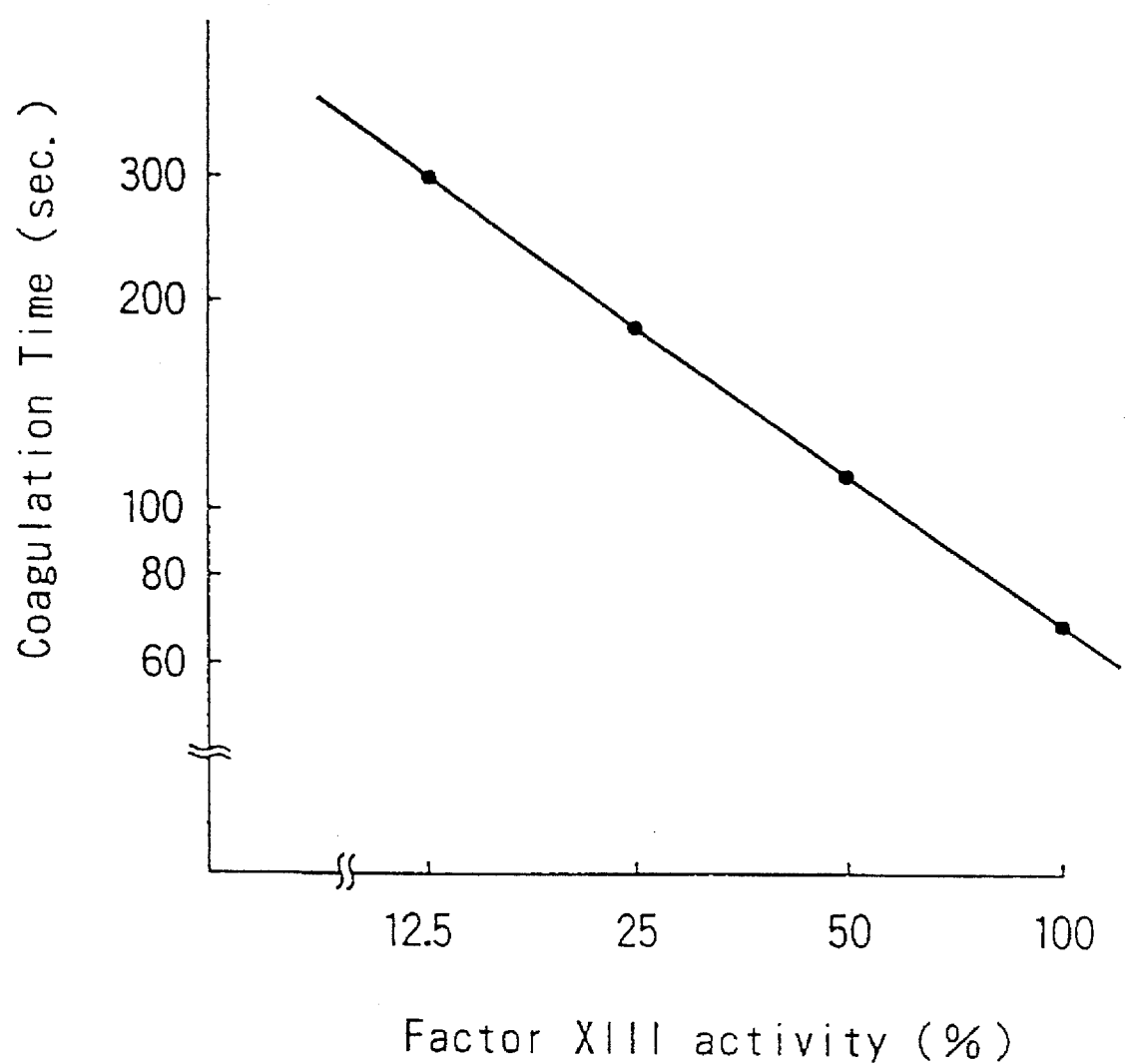
FIG. 1 is a graph showing the relationship between factor XIII activity and coagulation time (clotting time) determined using various concentrations of samples by the method 1 wherein fibrinogen is not used as the reagent in below Example 3.

The present invention provides a method of determining factor XIII activity (hereinafter referred to as the method 1) which comprises:

mixing a sample and a fibrin precipitation inhibitor;

adding a thrombin solution;

determining the fibrin coagulation time in the presence of calcium ion; and comparing the coagulation time with the normal coagulation time to determine factor XIII activity in the sample.

The present invention also provides a method of determining factor XIII activity (hereafter referred to as the method 2) which comprises:

mixing a sample, fibrinogen and a fibrin precipitation inhibitor;

adding a thrombin solution;

determining the fibrin coagulation time in the presence of calcium ion; and comparing the coagulation time with the normal coagulation time to determine factor XIII activity in the sample.

DETAILED DESCRIPTION OF THE INVENTION

The action of the factor XIII is to form fibrin clots in living bodies. The formation is by cross-linking reaction using fibrin formed in blood as the substrate. According to the method 1, the entire ability to form fibrin clots in blood is shown and it determines factor XIII activity. According to the method 2, the more accurate net activity of the factor XIII can be determined by supplemented fibrinogen as the reagent as well as fibrinogen in the sample containing the factor XIII.

In the determination method of the present invention, unlike prior art methods, factor XIII activity is determined by determining the coagulation time required for fibrin clot precipitation. That is, there is no prior art method wherein the coagulation time depending upon factor XIII activity is determined for the determination of the reaction converting fibrinogen into fibrin by thrombin followed by cross-linking of the fibrin by the activated factor XIII to form fibrin clots.

For example, in the method by determining coagulation time (e.g., determination of prothrombin time which is a screening test of coagulation reactions in extrinsic system, or determination of activated partial thromboplastin time which is a screening test of coagulation reactions in intrinsic system), fibrin is precipitated regardless of factor XIII activity and the coagulation time is determined (U.S. Pat. No. 3,323,995; Medical Technology, Vol. 13, No. 7, p. 726–729 (1985, extra edition)). In the thrombin time method used as daily tests for the determination of the fibrinogen amount, thrombin is added to fibrinogen (sample) to determine the time required for fibrin formation. Also in the method, the coagulation time is determined regardless of the presence of the factor XIII. That is, when fibrinogen is converted into fibrin by thrombin, fibrin is polymerized to form precipitates, and the coagulation time is determined. Therefore, the coagulation time in the blood coagulation reaction is determined independent of factor XIII activity.

As described above, when a thrombin solution is added to a fibrinogen solution, coagulation independent of the factor XIII occurs. For example, when a thrombin solution (100 NIHU/ml, 100 μl) is added to a fibrinogen solution (2 mg/ml, 200 μl), fibrin is precipitated and coagulated within 10 seconds in spite of the absence of the factor XIII. Therefore, the factor XIII cannot be determined as it is. In the present invention, factor XIII activity is determined by inhibiting the fibrin precipitation and determining the coagulation time in the system in which coagulation occurs depending upon factor XIII activity.

In this respect, the above JP-A 1-309700 discloses determination of factor XIII activity by adding a fibrin coagulation inhibitor (glycine-proline-arginine-proline) to remove effects of fibrinogen-fibrin. The detection is carried out by determining the resulting ammonia. This determination is completely different from the method of the present invention wherein the coagulation time method is used for the determination.

The sample and reagents used in the method of the present invention are described in the following.

The Sample

The sample to be used as the subject of the method of the present invention is normally plasma, but may be whole blood. It is drawn from subjects, and plasma is collected.

The Fibrin Precipitation Inhibitor

The present inventors has now found conditions inhibiting fibrin precipitation, namely conditions under which fibrinogen is converted into fibrin by thrombin and the resulting fibrin is not precipitated (polymerized) or coagulated for as long as possible, and conditions under which the factor XIII is activated by thrombin and calcium ion and the activated factor XIII can cross-link fibrin. The present invention has been made based on such findings.

In the specification, a fibrin precipitation inhibitor means a substance which provides conditions inhibiting fibrin precipitation and conditions under which factor XIII activity is exhibited.

The fibrin precipitation inhibitor in the present invention is not specifically limited so long as it has fibrin precipitation inhibitory activity. Examples thereof include sodium ion, potassium ion, calcium ion, magnesium ion, iodide ion, chloride ion and the like (calcium ion is an essential factor for activation of the factor XIII but can also be used as the fibrin precipitation inhibitor) of sodium iodide, potassium iodide, calcium chloride, magnesium chloride and the like; protein denaturing agents such as urea, SDS (Sodium Dodecyl Sulfate); SH reagents such as dithiothreitol (DTT), dithioerythritol (DTE), 2-mercaptoethanol and β-thiodiglycol; chelating agents such as EDTA (Ethylenediamine tetraacetic Acid) and EGTA (Ethylene Glycol Bis(β-aminoethylether)-N,N,N',N'-tetraacetic Acid); peptides such as glycine-proline-arginine-proline; tetraethylammonium chloride; benzyltriethylammonium chloride; ammonium sulfate; sodium cholate; potassium ferricyanide; dimethyl sulfoxide; dimethylformamide; ethylene glycol; hexamethylene glycol and the like. In the present invention, these fibrin precipitation inhibitors can be used alone or in combination of the two or more of them.

The inhibitory activity of the fibrin precipitation inhibitor may vary with the pH of the reaction mixture. Preferably, it is used at a pH at which the precipitation inhibitory activity is sufficiently exhibited. For example, as shown in Examples, when the fibrin precipitation inhibitory activity is sufficiently exhibited under weakly acidic conditions, a buffer is used to adjust the pH to weakly acidic regions. In these cases, the final pH of the reaction mixture is adjusted to 5.0 to 8.0, preferably 6.0 to 7.0. The concentration of the buffer is adjusted to 2 to 2000 mmol/l, preferably 20 to 400 mmol/l. Examples of the buffer for the pH adjustment include tris, barbital, imidazole, veronal, glycylglycine, MES, Bis-Tris, ADA, PIPES, HEPES, ACES, MOPUSO, BES, MOPUS and the like.

The concentration of each added material as the fibrin precipitation inhibitor in the reaction mixture is 0.1 to 5000 mmol/l in the case of ions such as sodium ion, potassium ion, calcium ion, magnesium ion, iodide ion and chloride ion from salts such as sodium iodide, potassium iodide, sodium chloride, potassium chloride, calcium chloride, magnesium chloride and the like. It is 0.1 to 3000 mmol/l in the case of urea, and 0.01 to 1.0% (w/v) in the case of SDS as protein denaturing agents. It is 0.1 to 1000 mmol/l in the case of DTT and DTE, 0.1 to 2000 mmol/l in the case of 2-mercaptoethanol, and 0.1 to 3000 mmol/l in the case of β-thiodiglycol as SH reagents. It is 0.1 to 500 mmol/l in the case of EDTA and EGTA as chelating agents. It is 0.01 to 10 mmol/l in the case of glycine-proline-arginine-proline as peptides. It is 0.1 to 5000 mmol/l in the case of tetraethylammonium chloride, 0.1 to 3000 mmol/l in the case of benzyltriethylammonium chloride, 0.1 to 2000 mmol/l in the case of ammonium sulfate, 0.01 to 10% (w/v) in the case of sodium cholate, 0.1 to 500 mmol/l in the case of potassium ferricyanide, 0.01 to 40% (v/v) in the case of dimethyl sulfoxide, 0.01 to 40% (v/v) in the case of dimethylformamide, 0.01 to 40% (v/v) in the case of ethylene glycol, and 0.1 to 5000 mmol/l in the case of hexamethylene glycol. Preferred concentrations of these materials can be appropriately selected depending upon the combination of the pH and each material.

As substances inhibiting fibrin coagulation (precipitation), peptides containing a glycine-prolineaginine residue, urea, benzyltriethylammonium chloride and tetraethylammonium chloride are known as substances affecting fibrin precipitation or dissolving the precipitated fibrin, and their acidity and ion strength are also known (Biochemistry, Vol. 19, 1013–1019, 1980; Blood, Vol 50,619– 624, 1977). However, these materials and the like were used only for a study of polymerization of fibrin with each other, preparation of fibrin monomers and dissolution of fibrin clots, and not for determination of factor XIII activity by the coagulation time method as in the present invention.

The Thrombin, Fibrinogen, Calcium Ion

In the determination method of the present invention, as the fibrinogen and thrombin, those derived from blood of humans, cattle, horses, goats or the like can be used. As the calcium ion, that derived from calcium salts such as calcium chloride, calcium gluconate or the like can be used. These reagents and fibrin precipitation inhibitors are each commercially available. The fibrinogen reagents, thrombin reagents and fibrin precipitation inhibiting reagents are used, if necessary, after pH adjustment. Examples of buffers for the pH adjustment include tris, barbital, imidazole, veronal, glycylglycine, MES, Bis-Tris, ADA, PIPES, HEPES, ACES, MOPUSO, BES, MOPS and the like. These buffers are also commercially available.

The concentration of each reagent can appropriately be selected. The amount of fibrinogen of the fibrinogen reagent is 0.01 to 100 mg/ml, preferably 0.5 to 10 mg/ml in the reaction mixture. Thrombin of the thrombin reagent is 1 to 20000 NIHU/ml, preferably 20 to 500 NIHU/ml in the reaction mixture. In general, the thrombin reagent is used in an amount of about 20 to 300 µl per 100 µl of a mixed solution of the sample, fibrinogen reagent and fibrin precipitation inhibiting reagent. The calcium ion can be formulated into any or all of the fibrinogen reagent, fibrin precipitation inhibiting reagent and thrombin reagent. The concentration thereof in the reaction mixture is 0.1 to 1000 mmol/l, preferably 5 to 100 mmol/l. The pH and concentration of the fibrinogen reagent and thrombin reagent and the kind of buffer can appropriately be selected.

In the determination according to the present invention, various materials can appropriately be added to the fibrinogen reagent, fibrin precipitation inhibiting reagent and thrombin reagent in order to remove effects of various materials, maintain the efficacy and quality of the reagents, prepare the reagents, and the like. Examples of the material to be added include antifibrinolytic drugs such as ε-aminocaproic acid, tranexamic acid, aprotinin and the like; heparin inhibiting substances such as Polybrene, protamine and the like; antiseptics such as sodium azide, gentamycin sulfate, thimerosal and the like; surfactants such as triton X-100, Tween 20 and the like; saccharides; amino acids; proteins such as albumin and the like; polyethylene glycol; glycerol and the like.

The concrete operations of the determination method of the present invention are described in the following.

In the method 1 of determining factor XIII activity wherein the fibrin reagent is not used, a given amount of a plasma sample or a diluted solution thereof and a fibrin precipitation inhibiting reagent are mixed, the resulting mixture is warmed at 15° to 45° C., normally 37° C. for 1 to 10 minutes, preferably 2 to 5 minutes, then the thrombin reagent is added, and the coagulation time is determined at the same temperature. The fibrin precipitation inhibiting reagent may be formulated into the thrombin reagent. In this case, only the sample is previously warmed. In the method 2, a given amount of a plasma sample or a diluted solution thereof, a fibrinogen reagent and a fibrin precipitation inhibiting reagent are mixed, the resulting mixture is warmed at 15° to 45° C., normally 37° C. for 1 to 10 minutes, preferably 2 to 5 minutes, then the thrombin reagent is added, and the coagulation time is determined at the same temperature. The fibrin precipitation inhibitor may be formulated into either or both of the fibrinogen reagent and thrombin reagent, or may be used as a separate reagent. In the case of the separate reagent, it is added to a mixed solution of a sample and a fibrinogen reagent before adding the thrombin reagent. The order of the addition is not specifically limited. The temperature and warming time are not strict in the determination method of the present invention. A reaction temperature selected from the above region can be used. Separately, normal plasma as a standard is diluted with a diluent or factor XIII-deficient plasma to various concentrations. The coagulation time is measured by the same manner and plotted against the dilution to obtain a calibration curve. Factor XIII activity in the sample is obtained as a ratio of it to factor XIII activity of the normal plasma.

When the sample is diluted, normally, physiological saline or a buffer of pH 5.5 to 8.5 such as Michaelis buffer, Tris-hydrochloric acid buffer, Owrenveronal buffer, imidazole buffer, HEPES, BES, MOPS or the like, i.e., Good's buffer or the like is used. The resulting diluted solution may contain fibrinogen or a fibrin precipitation inhibitor.

Thus, according to the determination method of the present invention, factor XIII activity can be determined accurately, rapidly and simply. That is, the above operations using the above reagents gives a coagulation time dependent on factor XIII activity in the sample, and factor XIII activity can be determined accurately only by using a simple conventional apparatus for determining blood coagulation time. The net time required for the determination is short and about 5 minutes.

Further, the present invention provides a kit of reagents for determining factor XIII activity by the coagulation time method which comprises thrombin, calcium ion and a fibrin precipitation inhibitor (corresponding to the method 1), and a kit of reagents for determining factor XIII activity by the coagulation time method which comprises fibrinogen, thrombin, calcium ion and a fibrin precipitation inhibitor (corresponding to the method 2). In the fibrinogen reagent, fibrin precipitation inhibitory reagent and thrombin reagent which are constitutional reagents of the kit of reagents, a part or all of the fibrin precipitation inhibiting reagent may be contained in the fibrinogen reagent and thrombin reagent. The calcium ion may be contained in any or each of the fibrinogen reagent, thrombin reagent and fibrin precipitation inhibiting reagent. The calcium ion may also be used as the fibrin precipitation inhibitor.

The kit of reagents for determining factor XIII activity of the present invention may be a mixture of the constitutional reagents or a combination of each constitutional reagent. The mixed reagent or each constitutional reagent together with an excipient can be dissolved in purified water or a buffer to a given concentration in the reaction mixture according to a conventional manner to obtain a dosage form which as it is can directly be subjected to the determination. Alternatively, they can be molded into a concentrated solution which is to be diluted to a desired concentration timely just before use. Further, they can also be molded into a form of lyophilized products. Among them, the form of lyophilized products is normally adopted and is reconstituted with purified water or a buffer just before use. Furthermore, each constitutional reagent can be molded into the same or different form.

The following reference examples and examples further illustrate the present invention in detail.

Reference Example 1

A solution (50 μl) of human plasma-derived fibrinogen (manufactured by Sigma, U.S.A., Fraction I)(15 mg/ml) dissolved in 0.3 mol/l sodium chloride was added to commercial controlled normal plasma, Caliplasma (registered trademark, manufactured by bio Mérieux, France) or factor XIII-deficient plasma (manufactured by Sigma, U.S.A.)(50 μl) as a sample. After addition of the specimen solution (50 μl), the resulting mixture was warmed at 37° C. for 2 minutes, followed by addition of a solution (100 μl) of thrombin (manufactured by bio Mérieux, France, a constitutional reagent of the fibrinogen kit)(100 NIHU/ml) dissolved in 20 mmol/l calcium chloride. The coagulation time was determined with an instrument for determining coagulation time, KC-4 (manufactured by Amelung). A buffer was added to the specimen solution (50 μl). The relationship between the kind and pH and the coagulation time was examined. The results are shown in Table 1 (the concentration and pH are those in the specimen solution).

TABLE 1

Coagulation time of the normal plasma and factor XIII-deficient plasma

| Buffer | Concentration | pH | Normal plasma | factor XIII-deficient plasma |
|---|---|---|---|---|
| H₂O | | | 3.6sec. | 3.7sec. |
| Tris-hydrochloric acid | 0.25 mol/l | 8.2 | 4.1 | 4.0 |
| | | 7.4 | 4.6 | 4.5 |
| | | 6.6 | 5.7 | 6.0 |
| HEPES | 0.25 mol/l | 8.2 | 3.5 | 3.6 |
| | | 7.4 | 4.1 | 4.1 |
| | | 6.6 | 4.8 | 4.8 |
| Bis-Tris | 0.2 mol/l | 7.0 | 4.4 | 4.4 |
| | | 6.6 | 6.9 | 7.0 |
| | | 6.2 | 11.3 | 11.3 |
| | | 5.8 | 19.6 | 17.6 |

The lowering of the pH prolonged the coagulation time of the normal plasma and the factor XIII-deficient plasma, and the fibrin precipitation was inhibited. However, no difference in the coagulation time was observed between the normal plasma and the factor XIII-deficient plasma.

EXAMPLE 1

A solution (50 μl) of human plasma-derived fibrinogen (15 mg/ml) dissolved in 0.3 mol/l sodium chloride and 0.2 mol/l HEPES (pH 7.0) was added to commercial controlled normal plasma, Caliplasma or factor XIII-deficient plasma (50 μl) as a sample. After addition of the specimen solution (50 μl), the resulting mixture was warmed at 37° C. for 2 minutes, followed by addition of a thrombin (100 NIHU/ml) solution (100 μl) in 20 mmol/l calcium chloride. The coagulation time was determined with an instrument for determining coagulation time, KC-4. Various materials were added to the specimen solution (50 μl) to examine the effects. The results are shown in Table 2 (the concentration at the addition was that in the specimen solution).

TABLE 2

Coagulation time of the normal plasma and factor XIII-deficient plasma

| Added material | Concentration | Normal plasma | factor XIII-deficient plasma |
|---|---|---|---|
| H₂O | | 3.9sec. | 4.0sec. |
| Urea | 5.0 mol/l | 75.8 | 91.9 |
| Sodium iodide | 1.5 mol/l | 73.0 | 90.4 |
| Potassium iodide | 1.5 mol/l | 111.5 | 164.9 |
| Magnesium chloride | 1.0 mol/l | 100.6 | 111.2 |
| SDS | 0.5% | 52.0 | 128.7 |
| Benzyltriethylammonium chloride | 0.5 mol/l | 171.8 | 198.7 |
| Sodium cholate | 5.0% | 96.8 | 104.8 |
| Gly—Pro—Arg—Pro | 3.0 mmol/l | 34.7 | 35.6 |
| DTT | 100 mmol/l | 8.5 | 8.7 |
| DTE | 100 mmol/l | 8.7 | 9.6 |
| EDTA | 50 mmol/l | 170.5 | 170.7 |
| EGTA | 50 mmol/l | 49.6 | 53.8 |

The addition of the various materials prolonged the coagulation time. Urea, sodium iodide, potassium iodide, magnesium chloride, SDS, benzyltriethylammonium chloride and sodium cholate showed not less than 5.0 seconds of the difference in the coagulation time between the normal plasma and the factor XIII-deficient plasma, namely the difference in the coagulation time depending upon the presence of factor XIII activity. Thus, effects as a fibrin precipitation inhibitor was observed. Under these conditions, little effect as a fibrin precipitation inhibitor was observed in Gly-Pro-Arg-Pro, DTT, DTE, EDTA and EGTA.

EXAMPLE 2

A solution (50 μl) of human plasma-derived fibrinogen (15 mg/ml) dissolved in 1.0 mol/l sodium chloride and 0.2 mol/l HEPES (pH 6.6) was added to commercial controlled normal plasma, Caliplasma or factor XIII-deficient plasma (50 μl) as a sample. After addition of the specimen solution (50 μl), the resulting mixture was warmed at 37° C. for 2 minutes, followed by addition of a solution (100 μl) of thrombin (100 NIHU/ml) dissolved in 40mmol/l calciumchloride and 0.2 mol/l HEPES (pH 6.6). The coagulation time was determined with an instrument for determining coagulation time, KC-4. Various materials were added to the specimen solution (50 μl) to examine the effects. The results are shown in Table 3 (the concentration at the addition was that in the specimen solution).

TABLE 3

Coagulation time of the normal plasma and factor XIII-deficient plasma

| Added material | Concentration | Normal plasma | factor XIII-deficient plasma |
|---|---|---|---|
| $H_2O$ | | 15.1sec. | 16.1sec. |
| Urea | 2.5 mol/l | 104.6 | 135.9 |
| Sodium iodide | 1.0 mol/l | 123.9 | 173.3 |
| Potassium iodide | 1.0 mol/l | 163.3 | 245.4 |
| Magnesium chloride | 0.5 mol/l | 83.6 | 111.4 |
| Calcium chloride | 0.4 mol/l | 79.4 | 110.4 |
| DTT | 0.1 mol/l | 44.4 | 58.7 |
| DTE | 0.1 mol/l | 42.1 | 51.7 |
| 2-Mercaptoethanol | 0.2 mol/l | 37.4 | 44.3 |
| β-dithioglycol | 0.5 mol/l | 32.7 | 40.7 |
| EDTA | 40 mmol/l | 88.3 | 124.1 |
| EGTA | 50 mmol/l | 143.3 | 191.3 |
| Gly—Pro—Arg—Pro | 1.0 mmol/l | 61.9 | 73.2 |
| Tetraethylammonium choride | 0.5 mmol/l | 78.7 | 99.3 |
| Benzyltriethylammonium chloride | 0.2 mmol/l | 125.2 | 147.6 |
| Ammonium sulfate | 1.0 mol/l | 20.5 | 30.3 |
| Sodium cholate | 2.0% | 96.3 | 105.5 |
| Potassium ferricyanide | 0.1 mol/l | 38.7 | 45.7 |
| Dimethyl sulfoxide | 40.0% | 138.6 | 165.5 |
| Dimethylformamide | 10.0% | 50.5 | 58.1 |
| Ethylene glycol | 40.0% | 63.1 | 79.1 |
| hexamethylene glycol | 1.0 mol/l | 124.5 | 166.0 |

Under weakly acidic conditions of high concentrations of sodium chloride and calcium chloride, the addition of the various materials prolonged the coagulation time. Urea, sodium iodide, potassium iodide, magnesium chloride, calcium chloride, DTT, DTE, 2-mercaptoethanol, β-dithioglycol, EDTA, EGTA, glycin-proline-arginine-proline, tetraethylammonium chloride, benzyltriethylammoniumchloride, ammonium sulfate, sodium cholate, potassium ferricyanide, dimethyl sulfoxide, dimethylformamide, ethylene glycol and hexamethylene glycol showed not less than 5.0 seconds of the difference in the coagulation time between the normal plasma and the factor XIII-deficient plasma, namely the difference in the coagulation time depending upon the presence of factor XIII activity. Thus, effects as a fibrin precipitation inhibitor was observed. In Example 2, the fibrin precipitation inhibiting effects were observed in many materials which were not found to have the effects in Example 1. The salt concentration, buffer concentration and pH are each different between Examples 1 and 2. The effects were observed at lower concentrations of the added materials in Example 2 than in Example 1.

EXAMPLE 3

Commercial controlled normal plasma, Caliplasma (its factor XIII activity was considered to be 100%) and factor XIII-deficient plasma (its factor XIII activity was considered to be 0%) were mixed to prepare samples having factor XIII activities of 100%, 50%, 25% and 12.5%, respectively. After adding a solution (50 μl) containing 3 mmol/l DTT and 0.4 mol/l sodium iodide as the fibrin precipitation inhibiting reagent to each sample (100 μl), the resulting solution was warmed at 37° C. for 2 minutes. Then, a solution (100 μl) of thrombin (100 NIHU/ml) dissolved in 80mmol/l calcium-chloride and 0.4 mol/l HEPES (pH 6.6) was added. The coagulation time was determined with an instrument for determining coagulation time, KC-4.

The results are shown in FIG. 1.

In the determination of factor XIII activity without using fibrinogen as the reagent (the method 1), a linear relationship was observed between factor XIII activity and the coagulation time on a log-log graph, and factor XIII activity was determined quantitatively.

EXAMPLE 4

Commercial controlled normal plasma, Caliplasma (its factor XIII activity was considered to be 100%) and factor XIII-deficient plasma (its factor XIII activity was considered to be 0%) were mixed to prepare samples having factor XIII activities of 100%, 50%, 25% and 12.5%, respectively. A solution (50 μl) of human plasma-derived fibrinogen (15 mg/ml) dissolved in 0.3 mol/l sodium chloride was added to each sample (50 μl). Then, a solution (50 μl) containing 40mmol/l DTT and 0.1 mol/l sodium iodide was added as the fibrin precipitation inhibiting reagent. The resulting solution was warmed at 37° C. for 2 minutes. Then, a solution (100 μl) of thrombin (100 NIHU/ml) dissolved in 40mmol/l calcium chloride and 0.4 mol/l HEPES (pH 6.6) was added. The coagulation time was determined with an instrument for determining coagulation time, KC-4.

Figure 2:
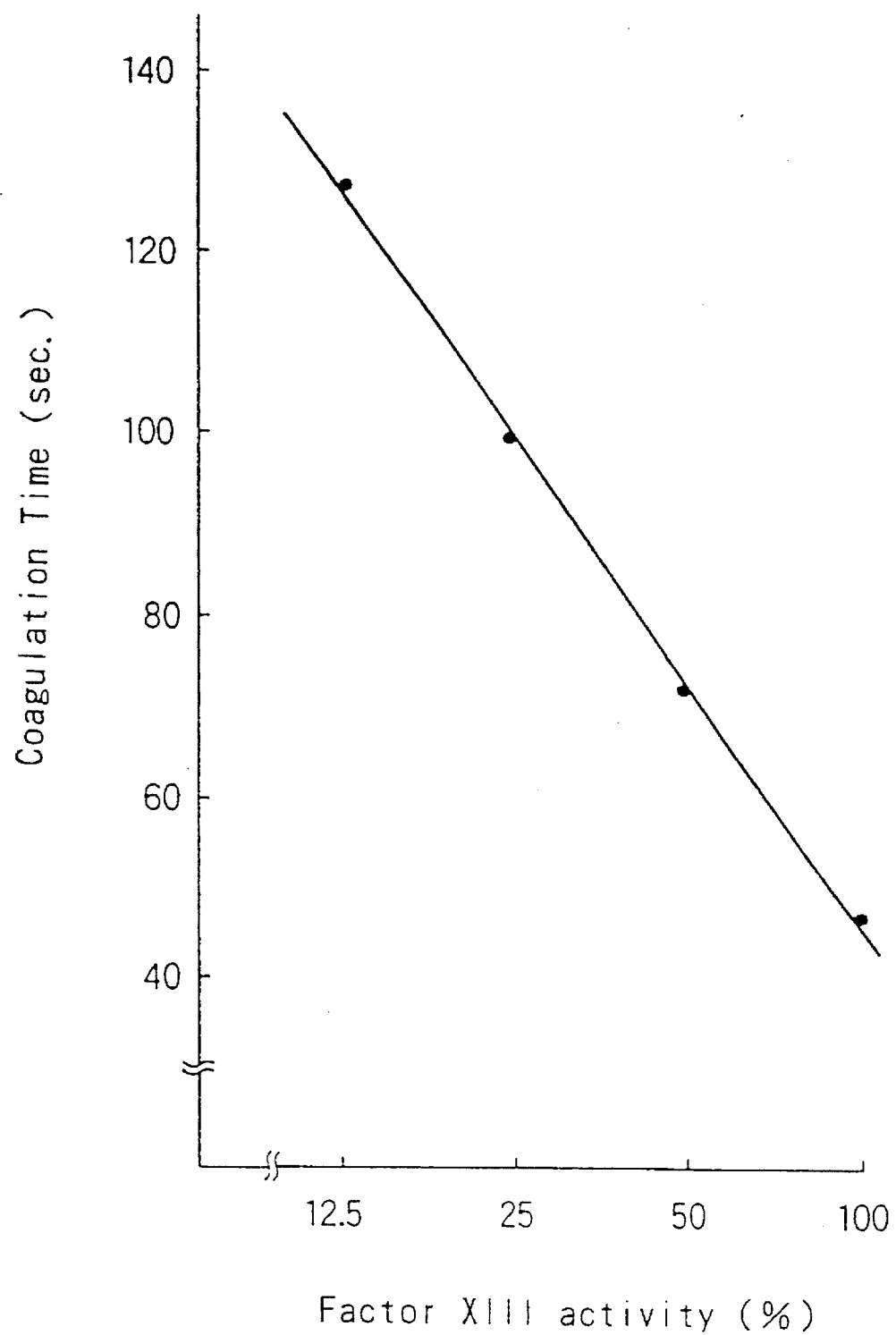
FIG. 2 is a graph showing the relationship between factor XIII activity and coagulation time (clotting time) determined using various concentrations of samples by the method 2 wherein fibrinogen is used as the reagent in below Example 4.

The results are shown in FIG. 2.

In the method using fibrinogen as the reagent (the method 2), a linear relationship was observed between factor XIII activity and the coagulation time on a semilogarithmic graph (the abscissa is the logarithmical axis), and factor XIII activity was determined quantitatively.

EXAMPLE 5

A thrombin solution comprising thrombin (concentration: 100 NIHU/ml), calcium ion (concentration: 80 mmol/l) and HEPES (0.4 mol/l, pH 6.6) and a solution of a fibrin precipitation inhibitor comprising DTT (3 mmol/l) and sodium iodide (0.4 mol/l) as the fibrin precipitation inhibitor were combined to obtain the kit of reagents for determining factor XIII activity of the present invention.

EXAMPLE 6

A fibrinogen solution comprising fibrinogen (concentration: 15 mg/ml) and sodium chloride (concentration: 0.3 mol/l), a thrombin solution comprising thrombin (concentration: 100 NIHU/ml), calcium ion (concentration: 40 mmol/l) and HEPES (0.4 mol/l, pH 6.6), and a solution of a fibrin precipitation inhibitor comprising DTT (40mmol/l) and sodium iodide (0.1 mol/l) as the fibrin precipitation inhibitor were combined to obtain the kit of reagents for determining factor XIII activity in the present invention.

As described above, the method of determining factor XIII activity of the present invention utilizes a reaction system similar to the living system, and provides high sensitivity for the determination and accurate value. The determination can be carried out with very simple operations and rapidly, and is a useful method applicable to usual clinical examinations.

We claim:

1. A method of determining factor XIII activity which comprises:

mixing a sample and a fibrin precipitation inhibitor;

adding a thrombin solution;

determining the fibrin coagulation time in the presence of calcium ion, wherein said fibrin coagulation results from conversion of fibrinogen in the sample to fibrin by thrombin and coagulation of the resulting fibrin by factor XIII; and comparing the coagulation time with the normal coagulation time to determine factor XIII activity in the sample.

2. A method of determining factor XIII activity which comprises:

mixing a sample, fibrinogen and a fibrin precipitation inhibitor;

adding a thrombin solution;

determining the fibrin coagulation time in the presence of calcium ion, wherein said fibrin coagulation results from conversion of fibrinogen in the sample and added fibrinogen to fibrin by thrombin and coagulation of the resulting fibrin by factor XIII; and comparing the coagulation time with the normal coagulation time to determine factor XIII activity in the sample.

3. A kit of reagents for determining factor XIII activity by the coagulation time method which comprises thrombin, calcium ion and a fibrin precipitation inhibitor, wherein said kit contains no glutamine-containing peptide.

4. A kit of reagents for determining factor XIII activity by the coagulation time method which comprises fibrinogen, thrombin, calcium ion and a fibrin precipitation inhibitor, wherein said kit contains no glutamine-containing peptide.

5. A kit of reagents for determining factor XIII activity by the coagulation time method which consists essentially of thrombin, calcium ion and a fibrin precipitation inhibitor.

6. A kit of reagents for determining factor XIII activity by the coagulation time method which consists essentially of fibrinogen, thrombin, calcium ion and a fibrin precipitation inhibitor.

* * * * *